(12) United States Patent
Cawood et al.

(10) Patent No.: US 10,647,999 B2
(45) Date of Patent: May 12, 2020

(54) PROMOTER

(71) Applicant: OXFORD GENETICS LIMITED, Oxford (GB)

(72) Inventors: Ryan Cawood, Oxford (GB); Richard Parker-Manuel, Oxford (GB); Weiheng Su, Oxford (GB)

(73) Assignee: Oxford Genetics Limited, Oxford Oxfordshire (GB)

( * ) Notice: Subject to any disclaimer, the term of this patent is extended or adjusted under 35 U.S.C. 154(b) by 0 days.

(21) Appl. No.: 16/080,765

(22) PCT Filed: Feb. 28, 2017

(86) PCT No.: PCT/GB2017/050537
§ 371 (c)(1),
(2) Date: Aug. 29, 2018

(87) PCT Pub. No.: WO2017/149292
PCT Pub. Date: Sep. 8, 2017

(65) Prior Publication Data
US 2019/0071692 A1 Mar. 7, 2019

(30) Foreign Application Priority Data
Mar. 1, 2016 (GB) .................................. 1603577.6

(51) Int. Cl.
| | | |
|---|---|---|
| *A61K 48/00* | (2006.01) | |
| *C07H 21/04* | (2006.01) | |
| *C12N 5/02* | (2006.01) | |
| *C12N 15/85* | (2006.01) | |
| *C07K 14/47* | (2006.01) | |
| *C12N 15/79* | (2006.01) | |

(52) U.S. Cl.
CPC .............. *C12N 15/85* (2013.01); *C07K 14/47* (2013.01); *C07H 21/04* (2013.01); *C12N 15/79* (2013.01); *C12N 2510/00* (2013.01); *C12N 2830/002* (2013.01); *C12N 2830/85* (2013.01)

(58) Field of Classification Search
CPC .... C12N 15/79; C12N 15/85; C12N 2510/00; C12N 2830/85; C07H 21/04
USPC ........... 424/93.21; 435/320.1; 536/23.1, 24.1
See application file for complete search history.

(56) References Cited

U.S. PATENT DOCUMENTS

| 2012/0244185 A1 | 9/2012 | Tucker et al. |
| 2013/0164326 A1 | 6/2013 | Tucker |
| 2014/0359901 A1 | 12/2014 | Scheirlinck et al. |

FOREIGN PATENT DOCUMENTS

| CN | 104630267 B | 5/2015 |
| WO | 2007/081336 A1 | 7/2007 |
| WO | 2008/073303 A2 | 6/2008 |
| WO | 2012/112603 A1 | 8/2012 |
| WO | 2013/063348 A1 | 5/2013 |
| WO | 2014/164869 A1 | 10/2014 |
| WO | 2016/022075 A1 | 2/2016 |

OTHER PUBLICATIONS

Nozaki et al., 2010, GeneSeq Accession No. AXX08059, computer printout, pp. 57-58.*
Wang et al., 2013 GeneSeq Accession No. BAX13701, computer printout, pp. 13-14.*
Juven-Gershon, T., et al., "Rational Design of a Super Core Promoter that Enhances Gene Expression", Nature Methods, Nov. 2006, vol. 3(11), pp. 917-922.
Ogawa, R., et al., "Construction of Strong Mammalian Promoters by Random cis-Acting Element Elongation", May 2007, BioTechniques, vol. 42, pp. 628-633, doi: 10.2144/000112436.
Schlabach, M.R., et al., "Synthetic Design of Strong Promoters", PNAS, Feb. 9, 2010, vol. 107(6), pp. 2538-2543, www.pnas.org/cgi/doi/10.1073/pnas.0914803107.
TornØe, J., et al., "Generation of a Synthetic Mammalian Promoter Library by Modification of Sequences Spacing Transcription Factor Binding Sites", Gene, Aug. 2002, vol. 297, pp. 21-32.
Apr. 7, 2016 (Apr. 7, 2016), "Plasmid pCMVssKZ-IntC3-CNLS targeting vector SEQ ID No. 30.", XP002769949, retrieved from EBI accession No. GSN:BCM12853, Database accession No. BCM12853 sequence.
Database Geneseq Mar. 9, 2017 (Mar. 9, 2017), "Plasmid PSIREN U6-shRNA-FF5 DNA SEQ ID No. 122.", XP002769950, retrieved from EBI accession No. GSN:BDN25293, Database accession No. BDN25293 sequence.
Dec. 11, 2008 (Dec. 11, 2008), "Human transcriptional regulatory element SEQ ID No. 5580.", XP002769951, retrieved from EBI accession No. GSN:ATN07640, Database accession No. ATN07640 sequence.
Dec. 11, 2008 (Dec. 11, 2008), "Human transcriptional regulatory element SEQ ID No. 6207.", XP002769952, retrieved from EBI accession No. GSN:ATN08267, Database accession No. ATN08267 sequence.
Combined Search and Examination Report under Sections 17 and 18(3), from the Intellectual Property Office, for GB1703224.4, dated Dec. 22, 2017, pp. 1-10.
International Search Report and Written Opinion, from the International Searching Authority, for PCT/GB2017/050537 dated May 29, 2017, pp. 1-22.
Balazs, A.B., et al., "Antibody-Based Protection Against HIV Infection by Vectored Immunoprophylaxis", Nature, vol. 481, pp. 81-84, (2012), doi: 10.1038/nature10660.
Maksimenko, O., et al., "Regulatory Elements in Vectors for Efficient Generation of Cell Lines Producing Target Proteins", Acta Naturae, vol. 7(3), pp. 15-26, (2015).

(Continued)

*Primary Examiner* — Shin Lin Chen
(74) *Attorney, Agent, or Firm* — McDonnell Boehnen Hulbert & Berghoff LLP

(57) ABSTRACT

The present invention relates to nucleic acid molecules which are capable of promoting transcription of operably-linked heterologous polynucleotides in mammalian cells. The invention also relates to expression vectors and host cells which comprise the nucleic acid molecules of the invention. Such expression vectors may be used to produce recombinant proteins, e.g. antibodies and lentiviral polypeptides.

15 Claims, 10 Drawing Sheets

Specification includes a Sequence Listing.

(56) References Cited

OTHER PUBLICATIONS

Altschul, S.F., et al., "Gapped BLAST and PSI-BLAST: A New Generation of Protein Database Search Programs", Nucleic Acids Research, 1997, vol. 25(17), pp. 3389-3402.
Ma, B., et al, "PatternHunter: Faster and More Sensitive Homology Search", Bioinformatics, Mar. 2002, vol. 18(3), pp. 440-445.
"BLAST: Basic Local Alignment Search Tool", Sep. 27, 2019. [Retrieved from the internet Dec. 4, 2019: <URL:https://blast.ncbi.nlm.nih.gov/Blast.cgi>].
"Searching the Trace Archive with Discontiguous MegaBlast", [Retrieved from the internet Dec. 4, 2019: <URL: https://www.ncbi.nlm.nih.gov/Web/Newsltr/FallWinter02/blastlab.html>].
European Office Action, from the European Patent Office, for European Patent Application No. 17712536.3, dated Sep. 20, 2019, pp. 1-11.
UK Office Action, from the Intellectual Property Office, for UK Application No. GB1703224.4, dated Sep. 30, 2019, pp. 1-3.
Singapore Written Opinion, from the Intellectual Property Office of Singapore, for Singapore Application No. 11201806782Q, dated Feb. 5, 2020, pp. 1-6.

\* cited by examiner

PROMOTER

CROSS-REFERENCE

This application is the US national phase under 35 U.S.C. § 371 of international application PCT/GB2017/050537, filed Feb. 28, 2017, which claims priority to Great Britain application 1603577.6, filed Mar. 1, 2016, which is incorporated by reference in its entirety.

FIELD OF INVENTION

The present invention relates to nucleic acid molecules which are capable of promoting transcription of operably-linked heterologous polynucleotides in mammalian cells. The invention also relates to expression vectors and host cells which comprise the nucleic acid molecules of the invention. Such expression vectors may be used to produce recombinant proteins, e.g. antibodies and lentiviral polypeptides.

BACKGROUND OF THE INVENTION

For transcription of a gene to occur, RNA polymerase must bind to the gene promoter and initiate transcription. In general, RNA polymerase I transcribes genes encoding ribosomal RNA; RNA polymerase II transcribes genes encoding messenger RNA, some small nuclear RNAs and microRNAs; while RNA polymerase III transcribes genes encoding transfer RNAs and other small RNAs.

Transcription is regulated in order to control when transcription occurs and how much RNA is created. Transcription of a gene by RNA polymerase can be regulated by at least five mechanisms:
(i) Specificity factors alter the specificity of RNA polymerase for a given promoter or set of promoters, making it more or less likely to bind to them (e.g. sigma factors used in prokaryotic transcription).
(ii) Repressors bind to the Operator (coding sequences on the DNA strand that are close to or overlapping the promoter region) impeding RNA polymerase's progress along the strand, thus impeding the expression of the gene.
(iii) Transcription factors position RNA polymerase at the start of a protein-coding sequence and then release the polymerase to transcribe the mRNA.
(iv) Activators enhance the interaction between RNA polymerase and a particular promoter, encouraging the expression of the gene. Enhancers are sites on the DNA helix that are bound by activators in order to loop the DNA bringing a specific promoter to the initiation complex.
(v) Silencers are regions of DNA sequences that, when bound by particular transcription factors, can silence expression of the gene.

A typical mammalian promoter consists of a 50-100 base pair core region to which the basic transcription machinery binds, and an enhancer region to which one or more transcriptional activator proteins (transactivators) may bind. The number and type of transactivators that are able to bind at an enhancer depends on which specific binding sites are present. The rate of initiation is governed by the number and type of transactivators actually bound at a promoter's enhancer. In addition to enhancers, there are silencers which, when bound by different transcription factors, lower gene expression.

Core promoters are made up of various different elements, of which there are two categories: canonical and non-canonical. Canonical core promoter elements include: TATA box, the initiator (Inr), the TFIIB recognition element (BRE), downstream promoter element (DPE) and downstream core element (DCE). These elements may be found within the core promoters of many but not all protein-coding genes. The TATA box (sequence TATAA) is usually found 20-30 bp upstream of the transcription start site (TSS) and acts as a binding site for the TFIID general transcription factor. When the Inr element (consensus sequence YYANT/AYY) is present, it encompasses the TSS, with the first A of the consensus being the first base of the transcript. BRE elements can be found both upstream of the TATA box (BREu consensus G/C G/C G/A CGCC) or downstream (BREd consensus G/A T T/A T/G T/G T/G T/G). Although not technically a canonical core promoter element, the CCAAT box (located between 50 and 100 bp upstream the TSS) is often included in this category. The CCAAT box also contributes to general transcription factor (TF) binding.

Non-canonical core promoter elements include the CpG island, the ATG desert and the transcription initiation platform (TIP). CpG islands generally span a 500-2000 bp stretch of DNA that contains a relatively high proportion of CpG dinucleotides. CpG dinucleotides would normally be methylated on the C residue, reducing transcription, but within CpG islands they remain unmethylated, promoting transcription. An ATG desert is a region of DNA with a lower frequency of ATG trinucleotides than surrounding regions. They extend approximately 1000 bp up and downstream of the TSS and are generally associated with promoters that do not contain TATA boxes.

A strong promoter is one that initiates transcription with a high frequency and can be a very useful tool. In biochemistry for example, strong promoters can be used to study transcription processes or to drive the production of recombinant proteins. Strong promoters are also useful in genetics: for example, they can be used to drive shRNA expression for gene knockdowns or for cDNA overexpression to deduce a protein's function.

A particularly potent promoter could also have medical applications: in a recombinant virus vaccine for example, higher antigen expression results in a better immune response.

The strongest promoters used in mammalian systems generally come from either constitutively expressed cellular genes or from viral genes. However, the promoters which are the strongest in terms of the expression levels of an associated gene are often the most cell-type dependent ones, i.e. they are limited in the types of cells in which they will work.

SUMMARY OF THE INVENTION

The present invention relates to nucleic acid molecules which are capable of promoting transcription of operably-linked heterologous polynucleotides in mammalian cells. The invention also relates to expression vectors and host cells which comprise the nucleic acid molecules of the invention. Such expression vectors may be used to produce recombinant proteins, e.g. antibodies and lentiviral polypeptides.

It is an object of the invention therefore to provide nucleic acid molecules which are capable of promoting transcription of an operably-linked heterologous polynucleotide at high levels and/or in a range of mammalian cells.

It is another object of the invention to provide expression vectors which comprise the nucleic acid molecules of the invention. Such expression vectors may be used to produce high levels of recombinant polypeptides, e.g. antibodies and lentiviral polypeptides.

In one embodiment, the invention provides a nucleic acid molecule comprising:
(a) a first polynucleotide having at least 80% nucleotide sequence identity to the nucleotide sequence set forth in SEQ ID NO: 1, SEQ ID NO: 2 or SEQ ID NO: 3, or a functional fragment of that first polynucleotide; and
(b) a second polynucleotide having at least 80% nucleotide sequence identity to the nucleotide sequence set forth in SEQ ID NO: 4, or a functional fragment of that second polynucleotide;
wherein (a) and (b) are joined 5'-3' in this order, and wherein said nucleic acid molecule is capable of promoting transcription of an operably-linked heterologous polynucleotide in a mammalian cell.

In a further embodiment, the invention provides an expression vector comprising a nucleic acid molecule of the invention.

In yet a further embodiment, the invention provides an expression vector comprising the nucleic acid molecule of the invention, wherein the nucleic acid molecule is operably-linked to a heterologous polynucleotide.

The invention also provides a mammalian host cell comprising an expression vector of the invention.

The invention also provides a kit comprising an expression vector of the invention.

DETAILED DESCRIPTION OF THE INVENTION

Figure 1:
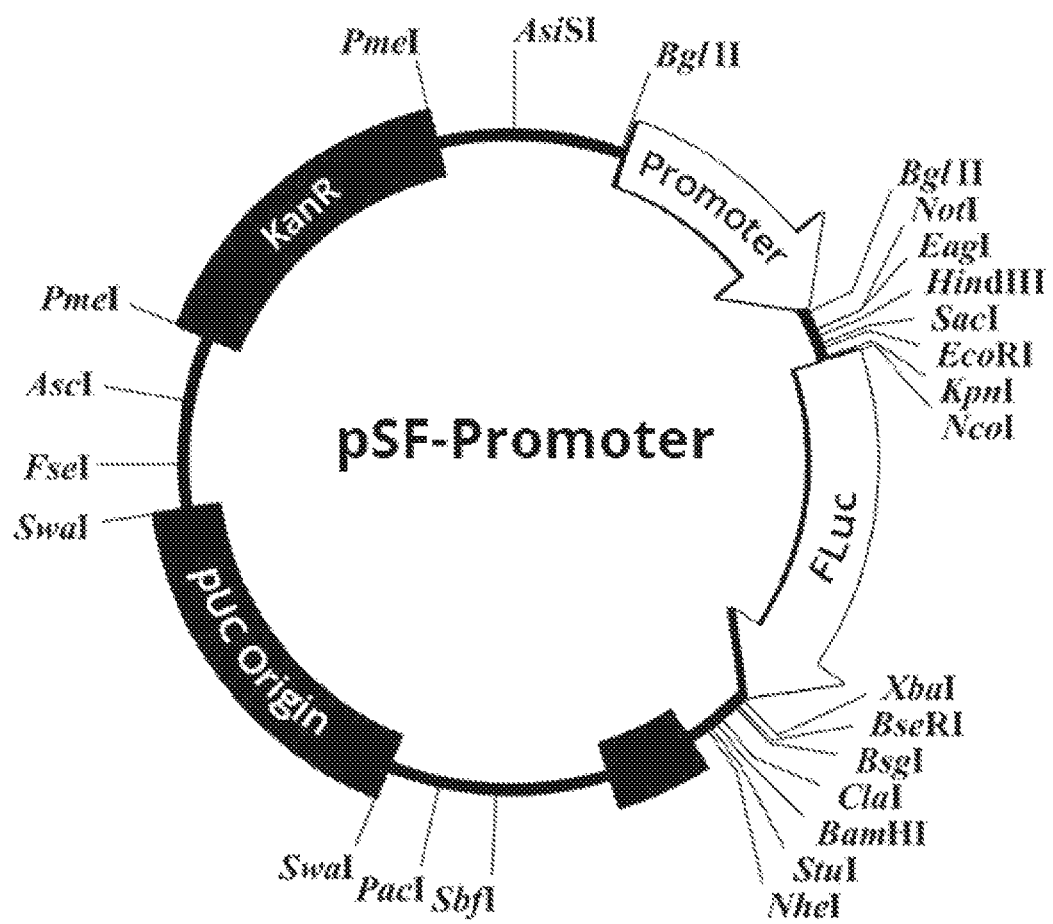
FIG. 1: pSF-SnapFast FLuc reporter vector background map.

In some embodiments, the nucleic acid molecule is an isolated nucleic acid molecule. The nucleic acid molecule of the invention is capable of promoting transcription of an operably-linked heterologous polynucleotide in a mammalian cell, i.e. it is acting as a promoter. In some embodiments, the nucleic acid molecule of the invention acts as a constitutive promoter.

The nucleic acid molecule of the invention comprises (a) a first polynucleotide having at least 80% nucleotide sequence identity to the nucleotide sequence set forth in SEQ ID NO: 1, SEQ ID NO: 2 or SEQ ID NO: 3. The sequences of SEQ ID NOs: 1-3 are given in the attached "Sequences" section. The first polynucleotide preferably has at least 85%, 90%, 95%, 96%, 97%, 98%, 99% or 100% nucleotide sequence identity to one of the nucleotide sequences set forth in SEQ ID NO: 1, SEQ ID NO: 2 or SEQ ID NO: 3. Most preferably, the first polynucleotide has the nucleotide sequence of SEQ ID NO: 1, SEQ ID NO: 2 or SEQ ID NO: 3.

The nucleic acid molecule of the invention may alternatively comprise a functional fragment of the first polynucleotide. As used herein, the term "functional fragment of that first polynucleotide" refers to a portion of the first polynucleotide that retains at least 20% (e.g. at least 30%, 40%, 50%, 60%, 70%, 75%, 80%, 85%, 90%, 95%, 98%, 99% or 100%) of the activity of the complete first polynucleotide in promoting the expression of an operably-linked heterologous polynucleotide. Methods for measuring and comparing the promoter activity of nucleic acid sequences are well known in the art, as discussed below.

Preferably, the functional fragment of the first polynucleotide is at least 50%, 60%, 70%, 80%, 90% or 95% of the length of the polynucleotide sequence set forth in SEQ ID NO: 1, SEQ ID NO: 2 or SEQ ID NO: 3.

The nucleic acid molecule of the invention also comprises: (b) a second polynucleotide having at least 80% nucleotide sequence identity to the nucleotide sequence set forth in SEQ ID NO: 4, or a functional fragment of that second polynucleotide. The sequence of SEQ ID NO: 4 is given in the attached "Sequences" section. Preferably, the second polynucleotide has at least 85%, 90%, 95%, 96%, 97%, 98%, 99% or 100% nucleotide sequence identity to the polynucleotide sequence set forth in SEQ ID NO: 4. Most preferably, the second polynucleotide has the polynucleotide sequence of SEQ ID NO: 4.

The nucleic acid molecule of the invention may alternatively comprise a functional fragment of the second polynucleotide. As used herein, the term "functional fragment of that second polynucleotide" refers to a portion of the second polynucleotide that retains at least 20% (e.g. at least 30%, 40%, 50%, 60%, 70%, 75%, 80%, 85%, 90%, 95%, 98%, 99% or 100%) of the activity of the complete second polynucleotide in promoting the expression of an operably-linked heterologous polynucleotide. Methods for measuring and comparing the promoter activity of nucleic acid sequences are well known in the art, as discussed below. Preferably, the functional fragment of the second polynucleotide is at least 50%, 60%, 70%, 80%, 90% or 95% of the length of the polynucleotide sequence set forth in SEQ ID NO: 4.

SEQ ID NO: 4 comprises a Transcription Start Site (TSS): the +1 site (i.e. the first base to be transcribed) is the first T in the sequence TCAGATC; this occurs at the 3'-end of SEQ ID NO: 4. Everything downstream of the TSS will be transcribed into RNA.

It is preferred, therefore, that the second polynucleotide, or the functional fragment thereof, comprises the sequence TCAGATC.

In some preferred embodiments, the nucleic acid molecule comprises:
    (a) a first polynucleotide having the nucleotide sequence set forth in SEQ ID NO: 1, SEQ ID NO: 2 or SEQ ID NO: 3; and
    (b) a second polynucleotide having the nucleotide sequence set forth in SEQ ID NO: 4;
wherein (a) and (b) are joined 5'-3', and wherein said nucleic acid molecule is capable of promoting transcription of an operably-linked heterologous polynucleotide in a mammalian cell.

In some preferred embodiments, the nucleic acid molecule comprises:
    (a) a first polynucleotide having the nucleotide sequence set forth in SEQ ID NO: 1; and
    (b) a second polynucleotide having the nucleotide sequence set forth in SEQ ID NO: 4;
wherein (a) and (b) are contiguously joined 5'-3' in this order, and wherein said nucleic acid molecule is capable of promoting transcription of an operably-linked heterologous polynucleotide in a mammalian cell.

In some preferred embodiments, the nucleic acid molecule comprises:
    (a) a first polynucleotide having the nucleotide sequence set forth in SEQ ID NO: 2; and
    (b) a second polynucleotide having the nucleotide sequence set forth in SEQ ID NO: 4;
wherein (a) and (b) are contiguously joined 5'-3' in this order, and wherein said nucleic acid molecule is capable of promoting transcription of an operably-linked heterologous polynucleotide in a mammalian cell.

In some preferred embodiments, the nucleic acid molecule comprises:
    (a) a first polynucleotide having the nucleotide sequence set forth in SEQ ID NO: 3; and
    (b) a second polynucleotide having the nucleotide sequence set forth in SEQ ID NO: 4;
wherein (a) and (b) are contiguously joined 5'-3' in this order, and wherein said nucleic acid molecule is capable of promoting transcription of an operably-linked heterologous polynucleotide in a mammalian cell.

The invention also provides a nucleic acid molecule comprising:
    (a) a first polynucleotide having at least 80% nucleotide sequence identity to the nucleotide sequence set forth in SEQ ID NO: 1, SEQ ID NO: 2 or SEQ ID NO: 3, or a functional fragment of that first polynucleotide;
    (b) a second polynucleotide having at least 80% nucleotide sequence identity to the nucleotide sequence set forth in SEQ ID NO: 4, or a functional fragment of that second polynucleotide; and
    (c) a third polynucleotide having at least 80% nucleotide sequence identity to the nucleotide sequence set forth in SEQ ID NO: 5, SEQ ID NO: 6 or SEQ ID NO: 7, or a functional fragment of that third polynucleotide;
wherein (a), (b) and (c) are joined 5'-3' in this order, and wherein said nucleic acid molecule is capable of promoting transcription of an operably-linked heterologous polynucleotide in a mammalian cell.

The sequences of SEQ ID NOs: 5-7 are given in the attached "Sequences" section.

The third polynucleotide preferably has at least 85%, 90%, 95%, 96%, 97%, 98%, 99% or 100% nucleotide sequence identity to one of the nucleotide sequences set forth in SEQ ID NO: 5, SEQ ID NO: 6 or SEQ ID NO: 7. Most preferably, the third polynucleotide has the nucleotide sequence of SEQ ID NO: 5, SEQ ID NO: 6 or SEQ ID NO: 7.

The nucleic acid molecule of the invention may alternatively comprise a functional fragment of the third polynucleotide. As used herein, the term "functional fragment of that third polynucleotide" refers to a portion of the third polynucleotide that retains at least 20% (e.g. at least 30%, 40%, 50%, 60%, 70%, 75%, 80%, 85%, 90%, 95%, 98%, 99% or 100%) of the activity of the complete third polynucleotide in promoting the expression of an operably-linked heterologous polynucleotide. Methods for measuring and comparing the promoter activity of nucleic acid sequences are well known in the art, as discussed below.

Preferably, the functional fragment of the third polynucleotide is at least 50%, 60%, 70%, 80%, 90% or 95% of the length of the polynucleotide sequence set forth in SEQ ID NO: 5, SEQ ID NO: 6 or SEQ ID NO: 7.

In some preferred embodiments, the nucleic acid molecule comprises:
  (a) a first polynucleotide having the nucleotide sequence set forth in SEQ ID NO: 1, SEQ ID NO: 2 or SEQ ID NO: 3;
  (b) a second polynucleotide having the nucleotide sequence set forth in SEQ ID NO: 4; and
  (c) a third polynucleotide having the nucleotide sequence set forth in SEQ ID NO: 5, SEQ ID NO: 6 or SEQ ID NO: 7;
wherein (a), (b) and (c) are joined 5'-3' in this order, and wherein said nucleic acid molecule is capable of promoting transcription of an operably-linked heterologous polynucleotide in a mammalian cell.

In some preferred embodiments, the nucleic acid molecule comprises:
  (a) a first polynucleotide having the nucleotide sequence set forth in SEQ ID NO: 1;
  (b) a second polynucleotide having the nucleotide sequence set forth in SEQ ID NO: 4; and
  (c) a third polynucleotide having the nucleotide sequence set forth in SEQ ID NO: 5;
wherein (a), (b) and (c) are contiguously joined 5'-3' in this order, and wherein said nucleic acid molecule is capable of promoting transcription of an operably-linked heterologous polynucleotide in a mammalian cell.

In some preferred embodiments, the nucleic acid molecule comprises:
  (a) a first polynucleotide having the nucleotide sequence set forth in SEQ ID NO: 2;
  (b) a second polynucleotide having the nucleotide sequence set forth in SEQ ID NO: 4; and
  (c) a third polynucleotide having the nucleotide sequence set forth in SEQ ID NO: 6;
wherein (a), (b) and (c) are contiguously joined 5'-3' in this order, and wherein said nucleic acid molecule is capable of promoting transcription of an operably-linked heterologous polynucleotide in a mammalian cell.

In some preferred embodiments, the nucleic acid molecule comprises:
  (a) a first polynucleotide having the nucleotide sequence set forth in SEQ ID NO: 3;
  (b) a second polynucleotide having the nucleotide sequence set forth in SEQ ID NO: 4; and
  (c) a third polynucleotide having the nucleotide sequence set forth in SEQ ID NO: 7;
wherein (a), (b) and (c) are contiguously joined 5'-3' in this order, and wherein said nucleic acid molecule is capable of promoting transcription of an operably-linked heterologous polynucleotide in a mammalian cell.

As used herein, the term "heterologous polynucleotide" refers to a polynucleotide which encodes a desired mRNA or polypeptide. Examples of heterologous polynucleotides include those that encode polypeptides, e.g. viral or mammalian polypeptides.

In some preferred embodiments, the heterologous polynucleotide encodes a protein that enters the secretory pathway, e.g. a membrane-linked protein, a secreted antibody or other secreted protein. Cells expressing such heterologous polynucleotides would be particularly suited to continuous production of recombinant secreted proteins in a bioreactor or suspension culture vessel, where the product can be harvested from the culture medium without lysing the cells.

Other preferred heterologous polynucleotides are those that encode proteins that remain cell-associated, such as membrane proteins or cytoplasmic proteins, which can either be used in the context of the whole cell or harvested by cell lysis. In some embodiments, the heterologous polynucleotide encodes an antibody. In some other preferred embodiments of the invention, the heterologous polynucleotide codes for a viral polypeptide. Preferably, the viral polypeptide is a surface glycoprotein, e.g. VSV G. The VSV G polypeptide is a single pass membrane glycoprotein derived from the Vesicular Stomatitis virus. It mediates a broad infectious tropism. In other embodiments, the viral polypeptide is Gag-Pol, Rev or Tat. The term "Gag-Pol" refers to a retrovirus protein that is proteolytically cleaved to produce a functional reverse transcriptase, integrase, and protease and at least two proteins of structural importance for virus assembly. Preferably, the Gag-Pol sequence is from a lentivirus, most preferably from HIV. The Rev protein aids transport of virus genomes into the cytoplasm. Preferably, the Rev polypeptide sequence is from a lentivirus, most preferably from HIV. The Tat protein enhances the efficiency of viral transcription. Preferably, the Tat polypeptide sequence is from a lentivirus, most preferably from HIV.

The first, second, third (when present) and heterologous polynucleotides (when present) are joined in this order in a 5'-3' direction.

One or more linker nucleotides may be present in between the first and second, second and third, second and heterologous, and third and heterologous polynucleotides, e.g. 1, 2, 3, 4, 5, 6, 7, 8, 9 or 10 linker nucleotides. When present, such linker polynucleotides should not have a significant detrimental effect on the efficacy of the promoter fragment (as measured, for example, in a luciferase assay). Preferably, there are no linker nucleotides, i.e. preferably the first, second, third (when present) and heterologous polynucleotides (when present) are joined contiguously in this order in a 5'-3' direction.

The nucleic acid molecule is capable of promoting transcription of an operably-linked heterologous polynucleotide in a mammalian cell.

The heterologous polynucleotide will be operably placed at a position downstream (i.e. 3') to the first, second and third (when present) polynucleotides of the invention.

In the context of the present invention, the term "promoting transcription" is intended to mean that when a heterologous polynucleotide is operably attached or inserted downstream of the first, second and third (when present) polynucleotides of the present invention, an expression product of the heterologous polynucleotide is obtained.

In some embodiments of the invention, the nucleic acid molecule is capable of promoting transcription of an operably-linked heterologous polypeptide in a mammalian cell in an inducible manner, i.e. the nucleic acid molecule is an inducible promoter. The nucleic acid molecule may therefore comprise an element which is repressible or activatable. For example, versions of the promoters disclosed here could be modified to contain binding sites for a protein that can either repress or activate transcription, creating inducible forms. In one example of this, the promoters disclosed herein (preferably p565 or p565i) could be modified to contain between 2-7 binding sites for the tetracycline repressor protein, most preferably 2-3 sites. By inserting said binding sites, the tetracycline repressor protein will be enabled to bind to the promoter and in doing so prevent the assembly of the basal transcription factor machinery on the promoter and thereby prevent both transcription and translation. This would abrogate protein expression. In the presence of Doxycycline or Tetracycline, the Tetracycline repressor protein is no longer able to bind DNA, and therefore the repressor can no longer bind the promoters, and transcription and translation can proceed unencumbered. As such, the transcriptional activity of the promoter created can be said to be induced by the presence of either Doxycycline or Tetracycline and would therefore be classed as an inducible promoter.

The term "expression product" as used herein is intended to mean either or both of (i) RNA (e.g. hnRNA, mRNA, siRNA or miRNA) which is a transcribed product of the heterologous polynucleotide and (ii) a polypeptide which is a translated product of the heterologous polynucleotide.

The heterologous polynucleotide may be operably inserted downstream of the nucleic acid molecule of the present invention such that the 5'-terminal end of the heterologous polynucleotide is located in a region within 500 bp, 400 bp, 300 bp, 200 bp, 100 bp, 50 bp, 30 bp or 10 bp from the 3'-terminal end of the nucleic acid molecule of the present invention.

The level of transcription which has been promoted by the nucleic acid molecule of the invention may be assayed by any suitable method. For example, for such an assay, the heterologous polynucleotide may be a selection marker gene (e.g. a neomycin resistance gene or hygromycin B phosphotransferase gene) or an expression reporter gene (e.g. LacZ, GFP (Green Fluorescence Protein), luciferase genes, etc.). Preferably, confirmation of promoter activity may be accomplished by using a FLuc gene.

The transcriptional activity of the nucleic acid molecule of the invention may be measured by operably inserting a reporter gene, such as the FLuc gene, downstream of the nucleic acid molecule of the invention. The level of expression of firefly luciferase protein can then be used to indicate the level of transcription which is obtained. To achieve this, the required DNA (including the nucleic acid of the invention upstream of the Fluc gene) may be introduced into a plasmid which is then transfected into suitable recipient cells (e.g. 293A cells) and allowed to express the firefly luciferase protein. After 24 hours, the cells may be lysed and the luciferase in the cell lysate may be monitored using a luminometer by measuring its output of light in the presence of its luciferin substrate.

The nucleic acid molecule is capable of promoting transcription of an operably-linked heterologous polynucleotide in a mammalian cell. Preferred mammalian cells include mouse, rat, hamster, monkey and human cells. Examples of such cells include HEK cells and derivatives (e.g. HEK293, HEK293T, HEK293A), PerC6, 911, CHO, HCT116, HeLa, COS and VERO cells; cancer cells such as HepG2, A549, and MCF7; primary cells isolated from human or animal biopsies; and stem cells (including pluripotent cells such as embryonic stem cells and induced pluripotent stem (iPS) cells, as well as multipotent stem cells such as haematopoietic stem cells, mesenchymal stem cells, etc.).

Preferred human cells include HEK293, HEK293T and HEK293A cells; and human stem cells (including pluripotent cells such as embryonic stem cells and induced pluripotent stem (iPS) cells, as well as multipotent stem cells such as haematopoietic stem cells, mesenchymal stem cells, etc.).

In a further embodiment, the invention provides an expression vector comprising a nucleic acid molecule of the invention. Preferably, the expression vector is a plasmid or virus vector. Examples of mammalian expression vectors include the adenoviral vectors, the pSV and the pCMV series of plasmid vectors, vaccinia and retroviral vectors, as well as baculovirus. In some embodiments, the expression vector is a lentiviral vector.

The expression vector may additionally comprise one or more of the following: an origin of replication, a selectable marker, and a multiple cloning site.

In yet a further embodiment, the invention provides an expression vector comprising the nucleic acid molecule of the invention, wherein the nucleic acid molecule is operably-linked to a heterologous polynucleotide.

The invention also provides a mammalian host cell comprising an expression vector of the invention. The expression vector may be transfected into a host cell by any suitable method. Preferably, the host cell is a mammalian cell (e.g. a human cell), such as those mentioned above. Such host cells may be isolated cells.

The invention further provides a mammal whose genome comprises a nucleic acid molecule of the invention or an expression vector of the invention. Preferably, the nucleic acid molecule of the invention or an expression vector of the invention is inserted into the genome of the mammal in such a way that a heterologous polynucleotide which is operably linked to said nucleic acid molecule of the invention or which is operably inserted into said expression vector of the invention is expressed in one or more cells of the mammal. Preferably, the mammal is a mouse or rat. In some embodiments, the mammal is a non-human mammal.

The invention also provides a kit comprising an expression vector and/or host cell of the invention, optionally together with one or more additional components selected from the group consisting of:
(i) a helper plasmid (e.g. one containing a nucleotide sequence encoding a lentiviral polypeptide under regulatory control of a promoter of the invention);
(ii) a virus genome plasmid (e.g. one with a packaging signal which may be adapted for simple insertion of a required transgene);
(iii) a buffer solution;
(iv) a restriction enzyme;
(v) transfection media; and
(vi) mammalian cells.

Percentage amino acid sequence identities and nucleotide sequence identities may be obtained using the BLAST methods of alignment (Altschul et al. (1997), "Gapped BLAST and PSI-BLAST: a new generation of protein database search programs", Nucleic Acids Res. 25:3389-3402; and http://www.ncbi.nlm.nih.gov/BLAST). Preferably the standard or default alignment parameters are used.

Standard protein-protein BLAST (blastp) may be used for finding similar sequences in protein databases. Like other BLAST programs, blastp is designed to find local regions of similarity. When sequence similarity spans the whole sequence, blastp will also report a global alignment, which is the preferred result for protein identification purposes. Preferably the standard or default alignment parameters are used. In some instances, the "low complexity filter" may be taken off.

BLAST protein searches may also be performed with the BLASTX program, score=50, wordlength=3. To obtain gapped alignments for comparison purposes, Gapped BLAST (in BLAST 2.0) can be utilized as described in Altschul et al. (1997) Nucleic Acids Res. 25: 3389. Alternatively, PSI-BLAST (in BLAST 2.0) can be used to perform an iterated search that detects distant relationships between molecules. (See Altschul et al. (1997) supra). When utilizing BLAST, Gapped BLAST, PSI-BLAST, the default parameters of the respective programs may be used.

With regard to nucleotide sequence comparisons, MEGA-BLAST, discontiguous-megablast, and blastn may be used to accomplish this goal. Preferably the standard or default alignment parameters are used. MEGABLAST is specifically designed to efficiently find long alignments between very similar sequences. Discontiguous MEGABLAST may be used to find nucleotide sequences which are similar, but not identical, to the nucleic acids of the invention.

The BLAST nucleotide algorithm finds similar sequences by breaking the query into short subsequences called words. The program identifies the exact matches to the query words first (word hits). The BLAST program then extends these word hits in multiple steps to generate the final gapped alignments. In some embodiments, the BLAST nucleotide searches can be performed with the BLASTN program, score=100, wordlength=12.

One of the important parameters governing the sensitivity of BLAST searches is the word size. The most important reason that blastn is more sensitive than MEGABLAST is that it uses a shorter default word size (11). Because of this, blastn is better than MEGABLAST at finding alignments to related nucleotide sequences from other organisms. The word size is adjustable in blastn and can be reduced from the default value to a minimum of 7 to increase search sensitivity.

A more sensitive search can be achieved by using the newly-introduced discontiguous megablast page (www.ncbi.nlm.nih.gov/Web/Newsltr/FallWinter02/blast-lab.html). This page uses an algorithm which is similar to that reported by Ma et al. (Bioinformatics. 2002 March; 18(3): 440-5). Rather than requiring exact word matches as seeds for alignment extension, discontiguous megablast uses non-contiguous word within a longer window of template. In coding mode, the third base wobbling is taken into consideration by focusing on finding matches at the first and second codon positions while ignoring the mismatches in the third position. Searching in discontiguous MEGABLAST using the same word size is more sensitive and efficient than standard blastn using the same word size.

Parameters unique for discontiguous megablast are:
word size: 11 or 12; template: 16, 18, or 21; template type: coding (0), non-coding (1), or both (2).

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1: Recombinant Promoter Fragments

Recombinant promoter fragments were produced consisting of the sequences identified in Table 1.

TABLE 1

Sequences of recombinant promoter fragments

| Promoter Name | First Polynucleotide | Second Polynucleotide | Third Polynucleotide |
|---|---|---|---|
| p567 | SEQ ID NO: 3 | SEQ ID NO: 4 | |
| p567i | SEQ ID NO: 3 | SEQ ID NO: 4 | SEQ ID NO: 7 |
| p576 | SEQ ID NO: 2 | SEQ ID NO: 4 | |
| p576i | SEQ ID NO: 2 | SEQ ID NO: 4 | SEQ ID NO: 6 |
| p565 | SEQ ID NO: 1 | SEQ ID NO: 4 | |
| p565i | SEQ ID NO: 1 | SEQ ID NO: 4 | SEQ ID NO: 5 |

The first, second and third (when present) polynucleotides were joined contiguously in the above promoter fragments.

Example 2: Construction of Expression Vector Comprising Promoter

The reporter vector that was used in the Firefly Luciferase assays was constructed as follows.

Preparing the Vector

The SnapFast (SF) vector shown in FIG. 1 was used. The back-bone of the SnapFast vector consists of a pUC bacterial origin of replication, an ampicillin resistance gene and a multiple cloning site. A firefly luciferase coding sequence was cloned into the multiple cloning site between the NcoI and XbaI restriction sites (see FIG. 1). The luciferase coding sequence incorporates a Kozak ribosome binding site.

The reporter plasmid was linearized with BglII and then de-phosphorylated to prevent re-ligation of the vector backbone. The cut vector was isolated from uncut vector by gel extraction followed by column based purification. The recombinant promoter fragments (from Example 1) were then ligated into the BglII cut vector.

The vectors were transformed into a standard E. coli cloning strain and plated onto LB kanamycin selection plates resulting in one recombinant promoter per colony. Colonies were picked for mini scale-plasmid preparation. These promoter clones were used for transfections into HEK293 cells and subsequent luciferase expression assays.

Example 3: Assay for Promoter Activity

Materials and Methods

Plasmid DNA was purified from a colony from each recombinant promoter. The reporter vectors containing the recombinant promoters were individually transfected into HEK293 cells in several 96-well plates. The transfected cells were incubated at 37° C. for 24 hours. Each well was assayed for luciferase activity using the Luciferase Assay System kit (Promega, Wis., USA).

Briefly, each assay was performed as follows: Culture medium was removed from each well. 100 µl of reporter lysis buffer was added to the cells in each well. The microtitre plate(s) was the incubated for 30 minutes at −20° C. to lyse the cells, then the plate was thawed by incubating it for 30 minutes at room temperature. The cell lysates were homogenised by pipetting up and down. A 25 µl sample of each lysate was transferred into a luminometer tube. The luciferase assay reagent was reconstituted by adding luciferase assay buffer to it. Samples were analysed on a Lumat LB 9507 luminometer (EG&G Berthold). The luminometer was set to inject 25 µl of luciferase assay reagent and then record the light emitted for a duration of 2 seconds. The output of the luminometer was given in relative light units.

The recombinant promoters were compared against a selection of standard highly-expressing promoters.

Results

Figure 2:
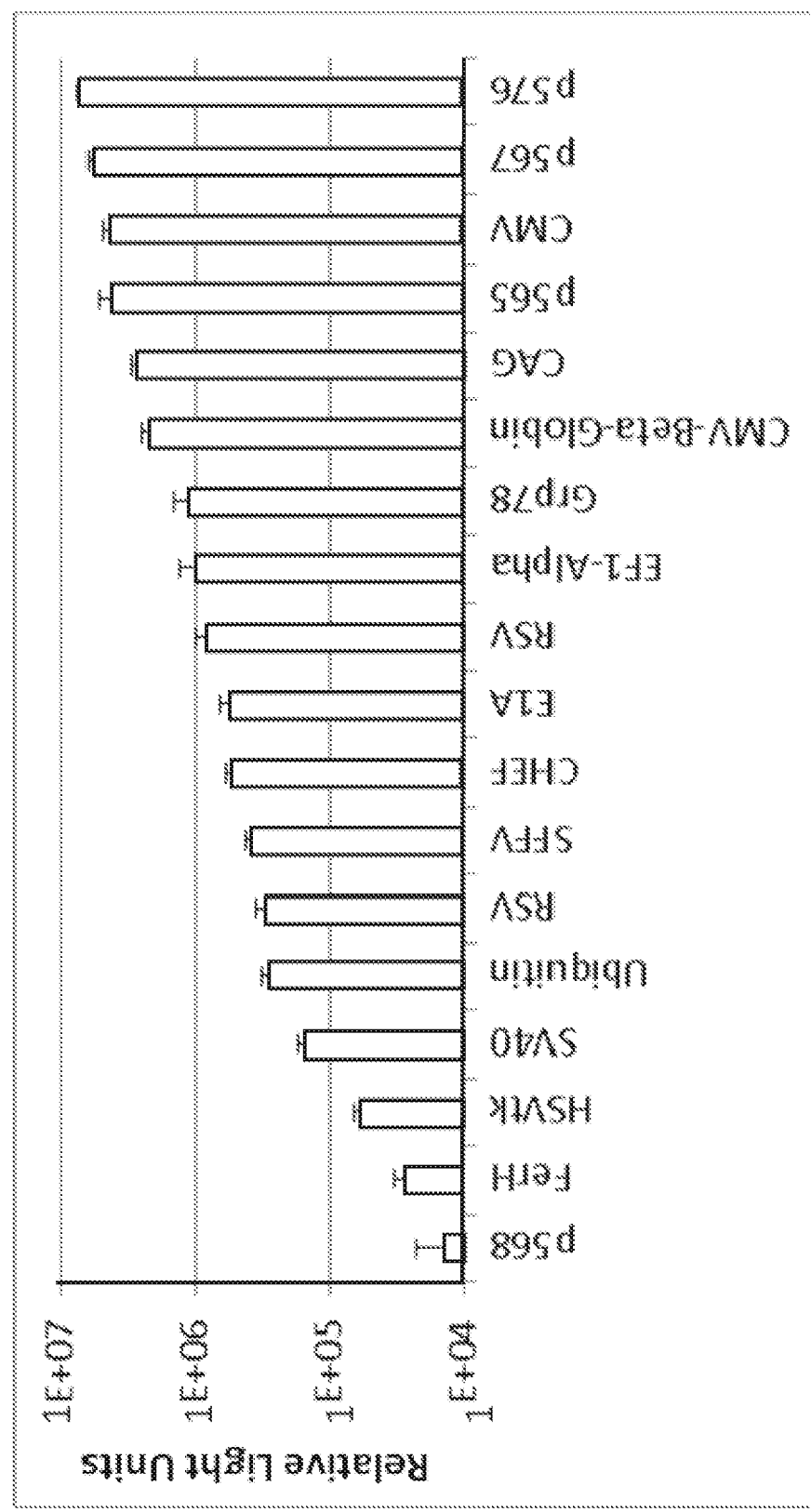
FIG. 2: Chart comparing recombinant promoter fragments with a range of standard promoters. Error bars show standard error. The experiment was performed in triplicate.

The results are shown in FIG. 2. The recombinant promoter fragments p567 and p576 performed better than CMV (the current gold standard) in this assay.

Example 4: Time Course Experiment

Figure 3:
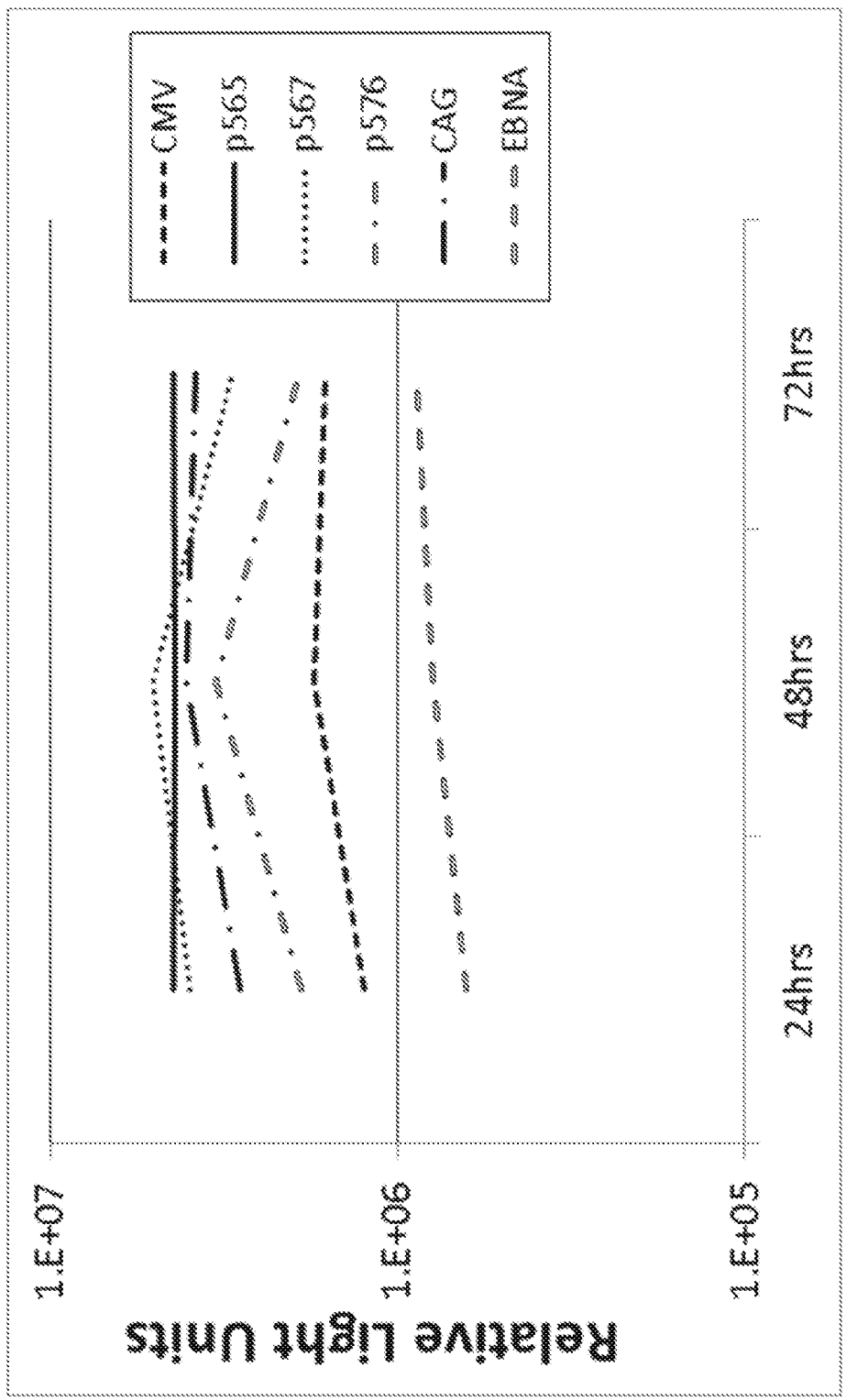
FIG. 3: Graph comparing the highest performing three recombinant promoters (p565, p567 and p576) with a range of standard high-expression promoters in a time course assay.

Three recombinant promoters (p565, p567 and p576) were selected for a time-course experiment. The results are shown in FIG. 3.

The results show that the recombinant promoters gave rise to consistently high luciferase expression over the course of 24 hours to 72 hours post-transfection.

Example 5: Expression Levels from the Recombinant Promoters

Figure 4:
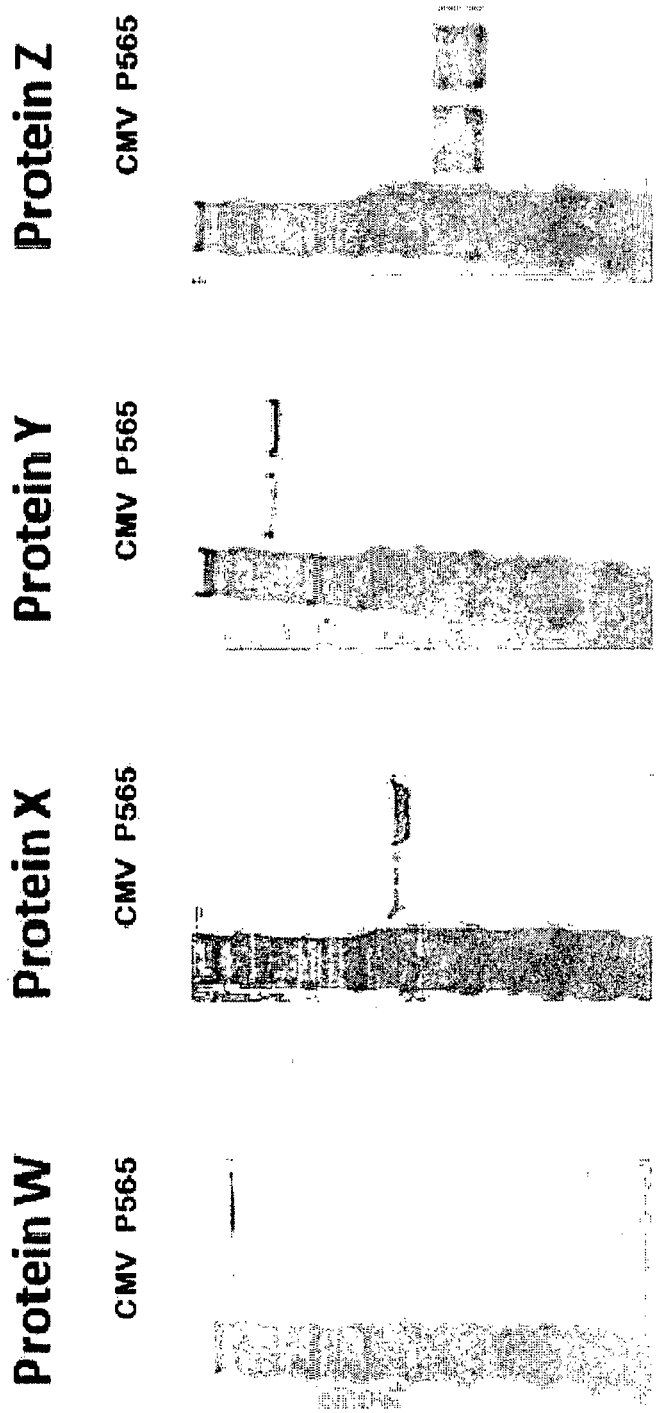
FIG. 4: Protein expression levels driven by recombinant promoter p565.

Protein expression levels driven by recombinant promoter p565 of the invention are shown in FIG. 4, with CMV promoter expression shown as a control. The p565 promoter was compared with a standard CMV promoter for expression of 4 different commercially useful antigens (Proteins 'W', 'X', 'Y' and 'Z'). For each antigen, the coding sequence was cloned downstream of either the CMV or p565 promoter in a vector equivalent to the one shown in FIG. 1.

On day 1, a 48-well microtiter plate was seeded with HEK293Ad cells at a density of 30,000 cells per well in a volume of 300 µl of serum free culture medium. On day 2, the cells in each well were transfected with 0.75 µg of DNA for each of the expression vectors. The cells were transfected using branched polyethylenimine (PEI) at a ratio of 3 µg for every µg of DNA. Prior to adding the DNA to the cells, it was incubated with the PEI for 20 minutes at room temperature to form DNA:PEI complexes. Three days after the transfection took place, the supernatant from each well was harvested and analysed for the quantity of antigen expressed by Western blot.

Example 6: Expression Levels in HEK293 Cells

Various human genes (see Table 2) were over-expressed from the CMV promoter or promoter P565i in human embryonic kidney cells (HEK293) by a method of transient transfection using branched PEI (25 kDa).

TABLE 2

Human genes which were overexpressed in HEK293 cells

| Protein | Ref |
|---|---|
| KLF4 | >sp\|O43474\|KLF4_HUMAN Krueppel-like factor 4 |
| XIAP | >sp\|P98170\|XIAP_HUMAN E3 ubiquitin-protein ligase XIAP |
| CYP2C1 | >sp\|P33261\|CP2CI_HUMAN Cytochrome P450 2C19 |
| CD4 | >sp\|P16070\|CD44_HUMAN CD44 antigen |
| Myc | >sp\|P01106\|MYC_HUMAN Myc proto-oncogene protein |
| LOX | >sp\|P28300\|LYOX_HUMAN Protein-lysine 6-oxidase |
| RAN | >sp\|P62826\|RAN_HUMAN GTP-binding nuclear protein Ran |
| FEV | >sp\|Q99581\|FEV_HUMAN Protein FEV |
| ABO | >sp\|P16442\|BGAT_HUMAN Histo-blood group ABO system transferase |
| GAPDH | >sp\|P04406\|G3P_HUMAN Glyceraldehyde-3-phosphate dehydrogenase |
| CDK | >sp\|P06493\|CDK1_HUMAN Cyclin-dependent kinase 1 |
| MyD88 | >sp\|Q99836\|MYD88_HUMAN Myeloid differentiation primary response protein |
| CRP | >sp\|P02741\|CRP_HUMAN C-reactive protein |
| NRAS | >sp\|P01111\|RASN_HUMAN GTPase NRas |
| IL10 | >sp\|P22301\|IL10_HUMAN Interleukin-10 |
| PTH | >sp\|P01270\|PTHY_HUMAN Parathyroid hormone |
| TNF | >sp\|P01375\|TNFA_HUMAN Tumor necrosis factor |
| INS | >sp\|P01308\|INS_HUMAN Insulin |
| CA1 | >sp\|P00915\|CAH1_HUMAN Carbonic anhydrase |
| JUN | >sp\|P05412\|JUN_HUMAN Transcription factor AP-1 |
| KRAS | >sp\|P01116\|RASK_HUMAN GTPase KRas |
| CD68 | >sp\|P34810\|CD68_HUMAN Macrosialin |
| CD14 | >sp\|P08571\|CD14_HUMAN Monocyte differentiation antigen CD14 |
| CD34 | >sp\|P28906\|CD34 HUMAN Hematopoietic progenitor cell antigen CD34 |
| PTEN | >sp\|P60484\|PTEN_HUMAN Phosphatidylinositol 3,4,5-trisphosphate 3-phosphatase and dual-specificity protein phosphatase PTEN |
| TP53 | >sp\|P04637\|P53_HUMAN Cellular tumor antigen p53 |
| NANOG | >sp\|Q9H950\|NANO6_HUMAN Homebox protein NANOG |
| RPE | >\|Q96AT9\|RPE_HUMAN Ribulose-phosphate 3-epimerase |

Figure 5:
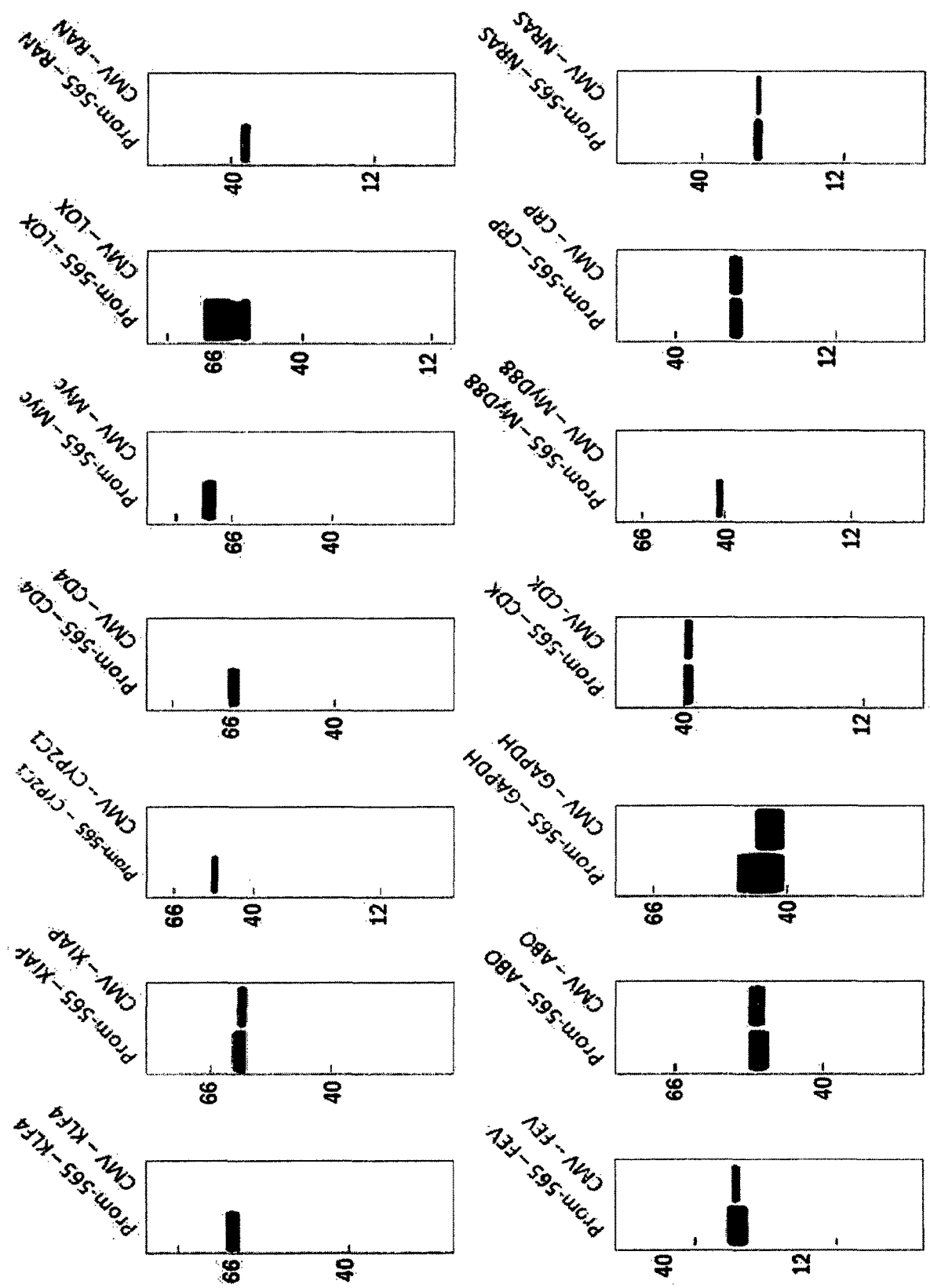
FIG. 5: Protein over expression in HEK293 cells from the CMV promoter and Oxford Genetics 'hybrid' prom-565 promoter using plasmid vector pcDNA3.1 and SnapFast Pro1v, respectively. (pcDNA3.1 is a protein expression vector available from Life Technologies. The plasmid vector contains the immediate early CMV promoter, the T7 promoter, the Bovine Growth Factor (BgH) poly adenylation signal alongside the F1 origin for making single stranded DNA and the SV40 promoter driving the expression of neomycin-kanamycin phosphotransferase (Aminoglycoside-3'-phosphotransferase) and the SV40 poly adenylation signal. If the pcDNA3.1 vector is to be used to express an exogenous protein of interest, the coding sequence of said protein would need to be inserted downstream (3') to the CMV and T7 promoters but upstream (5') of the BgH polyadenylation signal in the 5' to 3' orientation. The plasmid also contains an Ampicillin resistance gene for selection in bacterial cells. SnapFast ProV1 is a protein expression vector designed by Oxford Genetics Ltd that contains the promoter termed herein p565i followed by the SV40 polyadenylation signal. If the SnapFast ProV1 vector is to be used to express an exogenous protein of interest, the coding sequence of said protein would need to be inserted downstream (3') to the p565i promoter but upstream (5') of the SV40 polyadenylation signal in the 5' to 3' orientation. The plasmid also contains a Kanamycin resistance gene for selection in bacterial cells.) HEK293 cells were transfected with either pcDNA3.1 or SnapFast Pro1v expressing various FLAG-tagged fusion proteins. Protein levels from culture supernatant or cell lysate were determined by Western blot 72 hours post-transfection using Protein Simple Wes™ automated Western blot system. The FLAG-tagged fusion proteins were detected with mouse anti-FLAG primary antibody and secondary rabbit anti-mouse-IgG-HRP.
Figure 6:
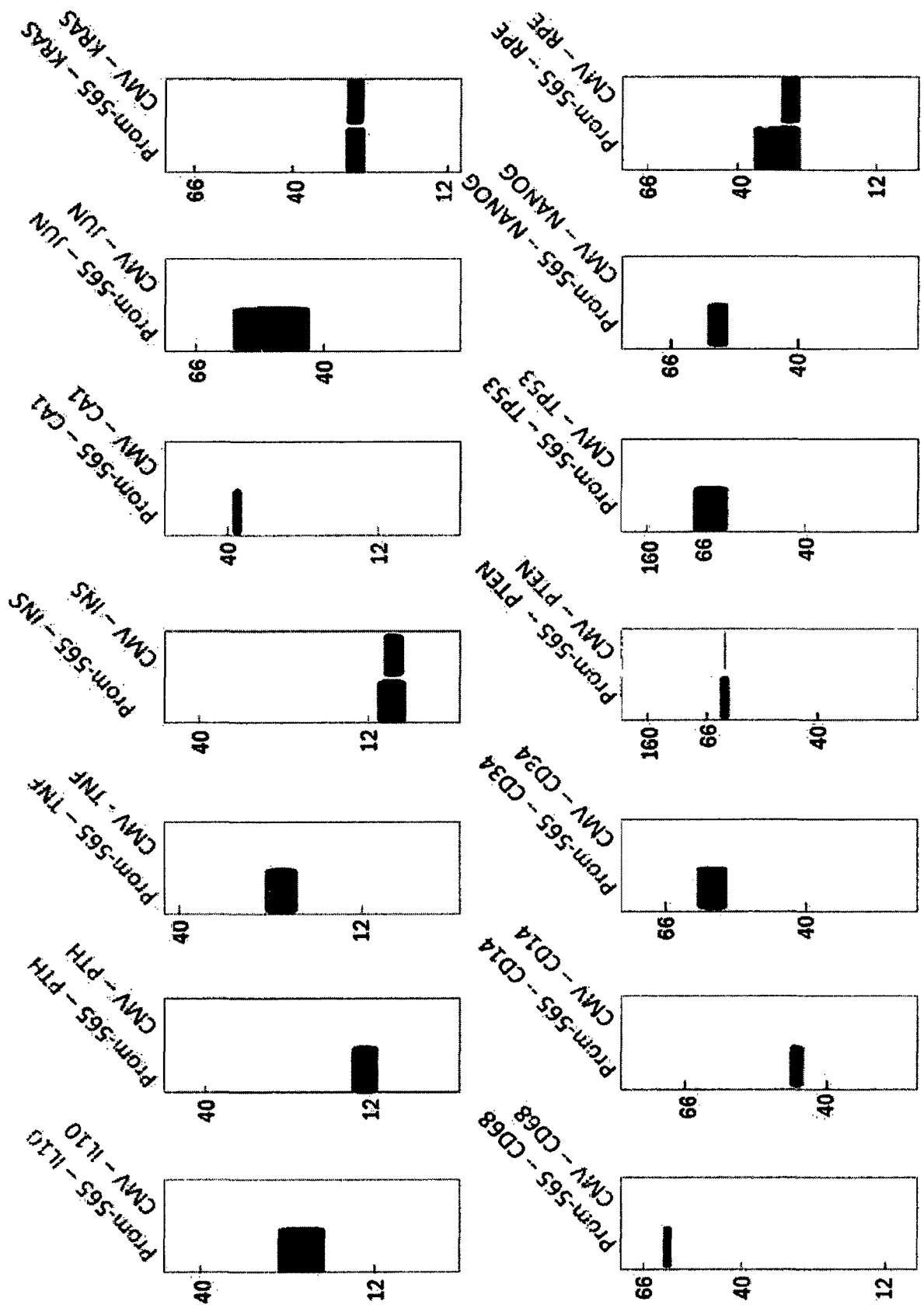
FIG. 6: Protein over expression in HEK293 cells from the CMV promoter and Oxford Genetics 'hybrid' prom-565 promoter using plasmid vector pcDNA3.1 and SnapFast Pro1v, respectively. HEK293 cells were transfected with either pcDNA3.1 or SnapFast Pro1v expressing various FLAG-tagged fusion proteins. Protein levels from culture supernatant or cell lysate were determined by Western blot 72 hours post-transfection using Protein Simple Wes™ automated Western blot system. The FLAG-tagged fusion proteins were detected with mouse anti-FLAG primary antibody and secondary rabbit anti-mouse-IgG-HRP.

HEK293 cells were seeded in tissue culture in a 48-well plate format (Sigma Aldrich) at a density of 25,000 cells per well for 24-hours prior to plasmid DNA transfection. Each plasmid DNA (750 ng) expressing FLAG tagged human gene from the CMV promoter or promoter P565i was mixed with branched PEI (25 kDA) at a ratio of 1:3, and the DNA:PEI complex were transiently transfected into each well of 48-well plate seeded HEK293 cells. Expression of each FLAG tagged human protein from transient transfection was analysed by automated western blotting (Wes™ Protein Simple) 72-hours post-transfection using mouse anti-FLAG primary antibody and secondary rabbit anti-mouse-IgG-HRP. The results are shown in FIGS. 5 and 6.

Example 7: Expression Levels in CHO Cells

Various human genes (see Table 3) were over-expressed from the CMV promoter or promoter P565i in CHO K1 cells by a method of transient transfection using branched PEI (25 kDa).

TABLE 3

Human genes which were overexpressed in CHO cells

| Protein | Ref |
|---|---|
| RAN | >sp\|P62826\|RAN_HUMAN GTP-binding nuclear protein Ran |
| RPE | >sp\|Q56AT9\|RPE_HUMAN Ribulose-phosphate 3-epimerase |
| FEV | >sp\|Q99581\|FEV_HUMAN Protein FEV |
| BCL2 | >sp\|P10415\|BCL2_HUMAN Apoptosic regulator Bcl-2 |
| CA1 | >sp\|P00915\|CAH1_HUMAN Carbonic anhydrase 1 |
| STAR | >sp\|P49675\|STAR_HUMAN Steroidogenic acute regulatory protein, mitochondrial |
| MYD88 | >sp\|Q99836\|MYD88_HUMAN Myeloid differentiation primary response protein |
| IGF1 | >sp\|P0S019\|IGF1_HUMAN Insulin-like growth factor 1 |
| ANG | >sp\|P03950\|ANGI_HUMAN Angiogenin |
| PI3 | >sp\|P19957\|ELAF_HUMAN Elafin |
| CXCL1 | >sp\|P09341\|GROA_HUMAN Growth-regulated alpha protein |
| INS1 | >sp\|P01308\|INS_HUMAN Insulin |
| PTMS | >sp\|P20962\|PTMS_HUMAN Parathymacin |
| CRP | >sp\|P02741\|CRP_HUMAN C-reactive protein |
| TNF | >sp\|P01375\|TNFA_HUMAN Tumor necrosis factor |
| BNDF | >\|P23560\|BNDF_HUMAN Brain-derived neurotrophic factor |
| FGF23 | >sp\|Q9GZV9\|FGF23_HUMAN Fibroblast growth factor 23 |
| APOE | >sp\|P02649\|APOE_HUMAN Apolipoprotein |
| CCL2 | >sp\|P13500\|CCL2_HUMAN C-C motif chemokine 2 |
| MAX | >sp\|P61244\|MAX_HUMAN Protein max |
| KRAS | >sp\|P01116\|RASK_HUMAN GTPase KRas |
| NRAS | >sp\|P01111\|RASN_HUMAN GTPase NRas |
| BAX | >sp\|Q07812\|BAX_HUMAN Apoptosis regulator BAX |
| RAC1 | >sp\|P63000\|RAC1_HUMAN Ras-related C3 botulinum toxin substrate 1 |
| RHOA | >sp\|P61586\|RHOA_HUMAN Transforming protein RhoA |
| EPO | >sp\|P01588\|EPO_HUMAN Erythropoietin |
| HMGB1 | >sp\|P09429\|HMGB1_HUMAN High mobility group protein B1 |

Figure 7:
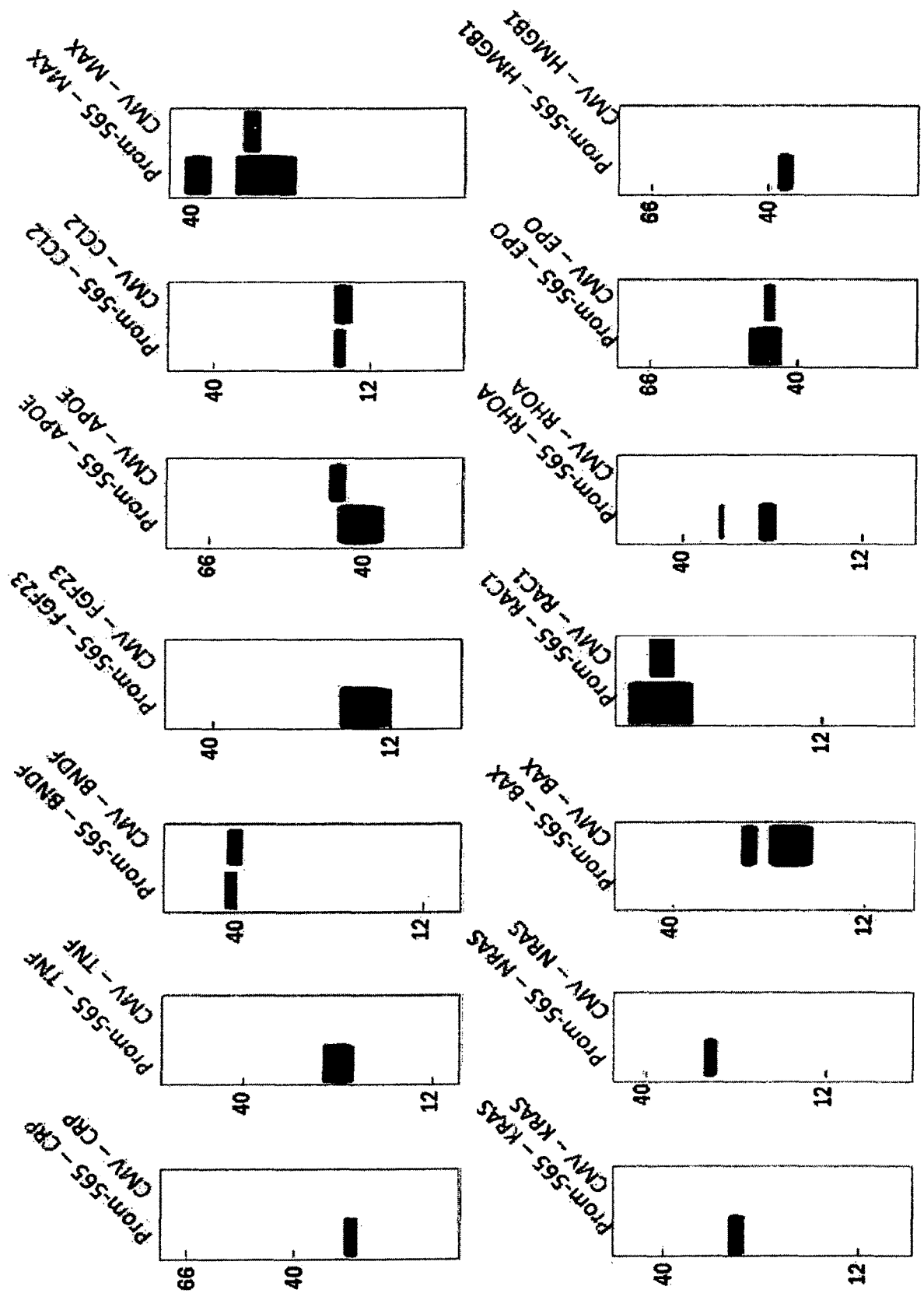
FIG. 7: Protein over expression in Chinese hamster ovary (CHO) cells from the CMV promoter and Oxford Genetics 'hybrid' prom-565 promoter using plasmid vector pcDNA3.1 and SnapFast Pro1v, respectively. CHO cells were transfected with either pcDNA3.1 or SnapFast Pro1v expressing various FLAG-tagged fusion proteins. Protein levels from culture supernatant or cell lysate were determined by Western blot 72 hours post-transfection using Protein Simple Wes™ automated Western blot system. The FLAG-tagged fusion proteins were detected with mouse anti-FLAG primary antibody and secondary rabbit anti-mouse-IgG-HRP.
Figure 8:
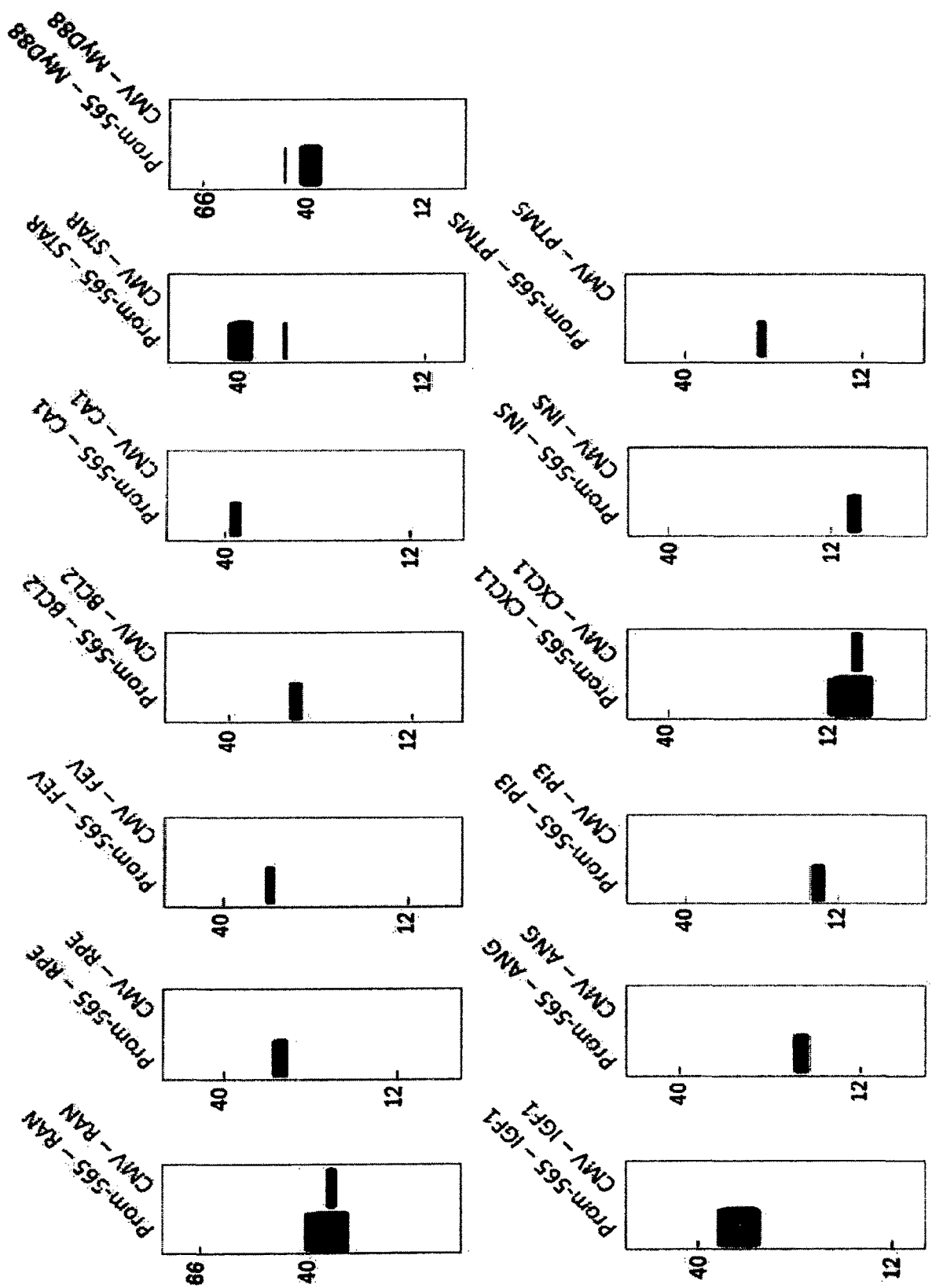
FIG. 8: Protein over expression in Chinese hamster ovary (CHO) cells from the CMV promoter and Oxford Genetics 'hybrid' prom-565 promoter using plasmid vector pcDNA3.1 and SnapFast Pro1v, respectively. CHO cells were transfected with either pcDNA3.1 or SnapFast Pro1v expressing various FLAG-tagged fusion proteins. Protein levels from culture supernatant or cell lysate were determined by Western blot 72 hours post-transfection using Protein Simple Wes™ automated Western blot system. The FLAG-tagged fusion proteins were detected with mouse anti-FLAG primary antibody and secondary rabbit anti-mouse-IgG-HRP.

CHO K1 cells were seeded in tissue culture in a 48-well plate format (Sigma Aldrich) at a density of 20,000 cells per well for 24-hours prior to plasmid DNA transfection. Each plasmid DNA (750 ng) expressing FLAG tagged human gene from the CMV promoter or promoter P565i was mixed with branched PEI (25 kDA) at a ratio of 1:3, and DNA:PEI complex were transiently transfected into each well of 48-well plate seeded CHO K1 cells. Expression of each FLAG tagged human protein from transient transfection was analysed by automated western blotting (Wes™ Protein Simple) 72-hours post-transfection using mouse anti-FLAG primary antibody and secondary rabbit anti-mouse-IgG-HRP. The results are shown in FIGS. 7 and 8.

Example 8: Expression Levels in HCT116 Cells

Green fluorescent protein (GFP) was expressed from the CMV, P565i, P565, P576, P567 promoters in HCT116 cells by a method of transient transfection using branched PEI (25 kDa).

Figure 9:
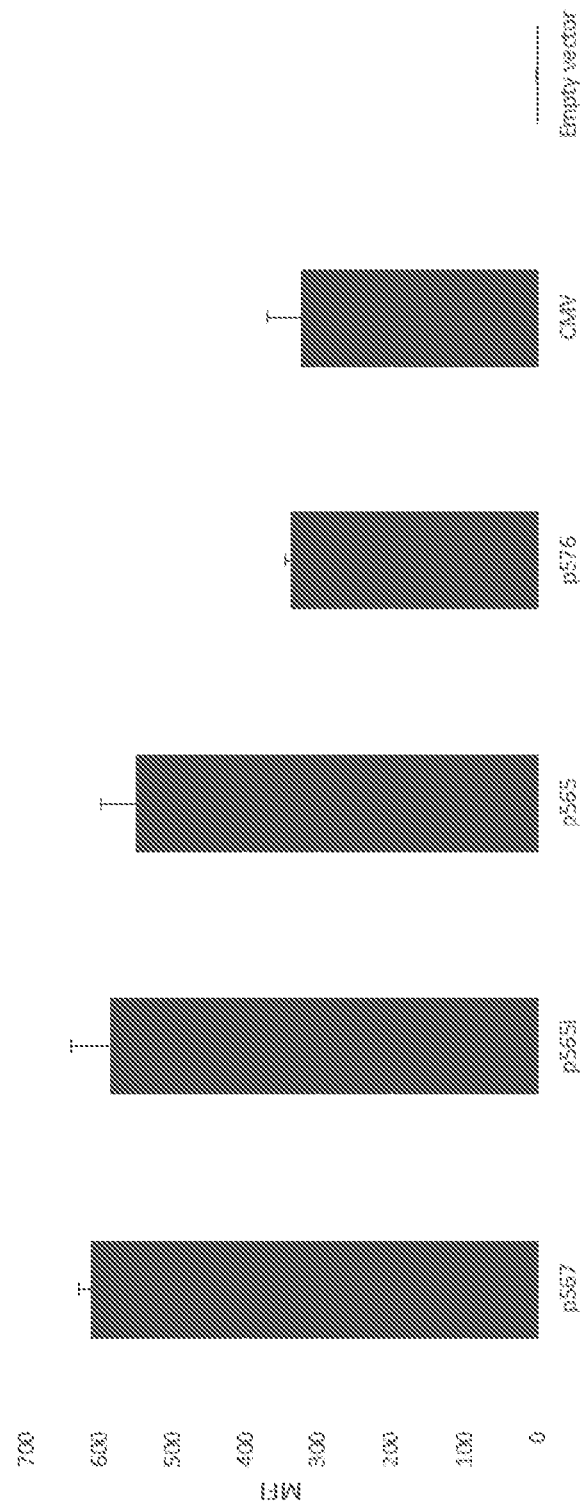
FIG. 9: Expression levels of GFP driven by promoters of the invention in HCT116 cells.

HCT116 cells were seeded in tissue culture treated 48-well plate format (Sigma Aldrich) at a density of 25,000 cells per well for 24-hours prior to plasmid DNA transfection. Each plasmid DNA (750 ng) expressing the enhanced green fluorescent protein from the CMV, P565i, P565, P576, or P567 promoter was mixed with branched PEI (25 kDA) at a ratio of 1:3, and the DNA:PEI complexes were transiently transfected into HCT116 cells. Enhanced green protein expression as determined by MFI of HCT116 cells was measured by flow cytometry 48-hours post-transfection. The results are shown in FIG. 9.

Example 9: Expression Levels in A549 Cells

Green fluorescent protein (GFP) was expressed from the CMV, P565i, P565, P576, P567 promoters in A549 cells by a method of transient transfection using branched PEI (25 kDa).

Figure 10:
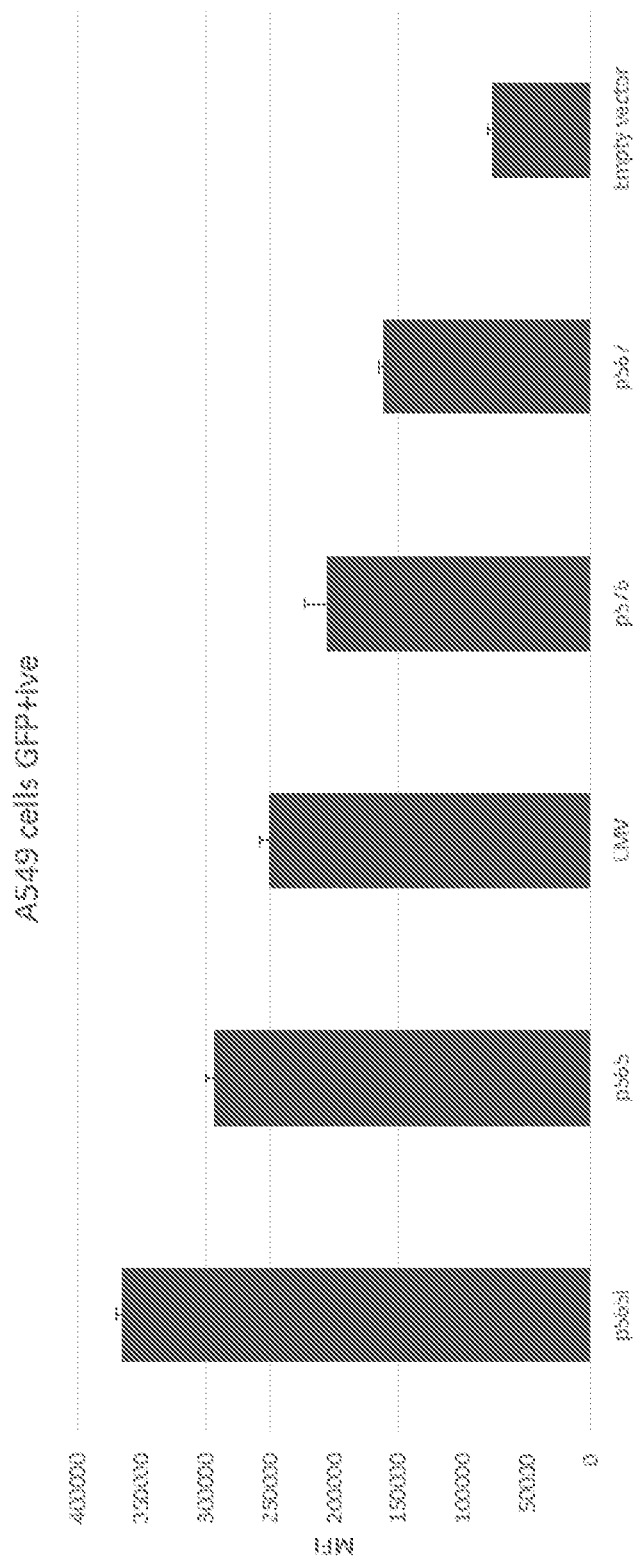
FIG. 10: Expression levels of GFP driven by promoters of the invention in A549 cells.

A549 cells were seeded in tissue culture treated 48-well plate format (Sigma Aldrich) at a density of 25,000 cells per well for 24-hours prior to plasmid DNA transfection. Each plasmid DNA (750 ng) expressing the enhanced green fluorescent protein from the CMV, P565i, P565, P576, or P567 promoter was mixed with branched PEI (25 kDA) at a ratio of 1:3, and the DNA:PEI complexes were transiently transfected into A549 cells. Enhanced green protein expression as determined by MFI of A549 cells was measured by flow cytometry 48-hours post-transfection. The results are shown in FIG. 10.

SEQUENCES

SEQ ID NO: 3
AGTAATCAATTACGGGGTCATTAGTTCATAGCCCATATATGGAGTTCCGC
GTTACATAACTTACGGTAAATGGCCCGCCTGGCTGACCGCCCAACGACCC
CCGCCC

SEQ ID NO: 2
CTACCGGGTAGGGGAGGCGCTTTTCCCAAGGCAGTCTGGAGCATGCGCTT
TAGCAGCCCCGCTGGGCACTTGGCGCTACACAAGTGGCCTCTGGCCTCGC
ACACATTCCACATCCACCGGTAGGCGTCAATGGAAAGTCCCTATTGGCGT
TACTATGGGAACATACGTCATT

SEQ ID NO: 1
CGTGAGGCTCCGGTGCCCGTCAGTGGGCAGAGCGCACATCGCCCACAGTC
CCCGAGAAGTTGGGGGGAGGGGTCGGCAATTGAACCGGTGCCTAGAGAAG
GTGGCGCGGGGTAAACTGGGAAAGTGATGTCGTGTACTGGCTCCCCCTTT
TTCCCGAGGGTGGGGGAGAACCGTATATAAGTGCACTAGTCGCCGTGAAC
GTCAATGGAAAGTCCCTATTGGCGTTACTATGGGAACATACGTCATTATT
GACGTCAATGACGGTAAATGGCCCGCCTGGCATTATGCCCAGTACATGAC
CTTATGGGACTTTCCTACTTGGCAGTACATCTACGTATTAGTCATCGCTA
TTACCATGCTGATGCCGTTTTGGCAGTACATCAATGGGCGTGGATAGCGG
TTTGACTCACGGGGATTTCCAAGTCTCCACCCC

SEQ ID NO: 4
ATTGACGTCAATGGGAGTTTGTTTTGGCACCAAAATCAACGGGACTTTCC
AAAATGTCGTAACAACTCCGCCCCATTGACGCAAATGGGCGGTAGGCGTG
TACGGTGGGAGGTCTATATAAGCAGAGCTGGTTTAGTGAACCGTCAGATC

SEQUENCES

SEQ ID NO: 7
GTTGTTCGCTTTGATAAACTTCCAGGATTCGGAGACAGTATTGAAGCTCA
GGTACAGAAATAATTTCACCTTTCTTTCTCTTTCTATTCAGTGTGGCACA
TCTGTAAACGTTCACTCTTCACTTAGAGACATCCTCAACCAAATCACCAA
ACCAA

SEQ ID NO: 6
GCCCAGGAAGTACACGAGAAGCTCCGAGGATTGGCTGAAGTCCAACGTCT
CTGATTGCGGTGGCTCAGAGCACCCGTATCATTTTGGAGGTGAGTGGCTT
TGGTTCCCGGCTGAGGTGGAGTGGGCTGAGGACTAGACTGAGCCCTCGGA
CATGGAGGTGGGGATGGGGCAGACTCATCCCATTCTTGACCAAGCCCTTG
TTCTGCTCCCTTCCCAGGCTCTGTGACTGGGGCAACCTGCAAGGAGCTGG
CCAGCCAGCCTGACGTGGACGGCTTCCTTGTGGGTGGTGCTTCCCTCAAG
CCCGAATTCGTGGACATCATCAACGCCAAACAA

SEQ ID NO: 5
TGAAGTTGGTGGTGAGGCCCTGGGCAGGTTGGTATCAAGGTTACAAGACA
GGTTTAAGGAGACCAATAGAAACTGGGCATGTGGAGACAGAGAAGACTCT
TGGGTTTCTGATAGGCACTGACTCTCTCTGCCTATTGGTCTATTTTCCCA
CCCTTAG

Sequence Listing Free Text

<223> Synthetic promoter element

The invention claimed is:

1. A nucleic acid molecule comprising:
   (a) a first polynucleotide having at least 80% nucleotide sequence identity to the nucleotide sequence set forth in SEQ ID NO: 1 or SEQ ID NO: 2; and
   (b) a second polynucleotide having at least 80% nucleotide sequence identity to the nucleotide sequence set forth in SEQ ID NO: 4;

wherein the first polynucleotide and the second polynucleotide are joined 5'-3' either contiguously or wherein 1-10 linker nucleotides are present between the first and second polynucleotides, and wherein said nucleic acid molecule is capable of promoting transcription of an operably-linked heterologous polynucleotide in a mammalian cell.

2. The nucleic acid molecule as claimed in claim 1, wherein the first polynucleotide has at least 85%, 90%, 95%, 96%, 97%, 98%, 99% or 100% nucleotide sequence identity to one of the nucleotide sequences set forth in SEQ ID NO: 1 or SEQ ID NO: 2.

3. The nucleic acid molecule as claimed in claim 1, wherein the second polynucleotide has at least 85%, 90%, 95%, 96%, 97%, 98%, 99% or 100% nucleotide sequence identity to the polynucleotide sequence set forth in SEQ ID NO: 4.

4. The nucleic acid molecule as claimed in claim 1, wherein the nucleic acid molecule comprises:
   (a) the first polynucleotide having the nucleotide sequence set forth in SEQ ID NO: 1 or SEQ ID NO: 2; and
   (b) the second polynucleotide having the nucleotide sequence set forth in SEQ ID NO: 4.

5. The nucleic acid molecule as claimed in claim 1, further comprising:
   (c) a third polynucleotide having at least 80% nucleotide sequence identity to a nucleotide sequence set forth in SEQ ID NO: 5, SEQ ID NO: 6 or SEQ ID NO: 7;
wherein the first polynucleotide, the second polynucleotide and the third polynucleotide are joined 5'-3' in this order either contiguously or wherein 1-10 linker nucleotides are present between the first, second and/or third polynucleotides, and wherein said nucleic acid molecule is capable of promoting transcription of an operably-linked heterologous polynucleotide in a mammalian cell.

6. The nucleic acid molecule as claimed in claim 5, wherein the third polynucleotide has at least 85%, 90%, 95%, 96%, 97%, 98%, 99% or 100% nucleotide sequence identity to one of the nucleotide sequences set forth in SEQ ID NO: 5, SEQ ID NO: 6 or SEQ ID NO: 7.

7. The nucleic acid molecule as claimed in claim 5, wherein the nucleic acid molecule comprises:
   (a) the first polynucleotide having the nucleotide sequence set forth in SEQ ID NO. 1 or SEQ ID NO. 2;
   (b) the second polynucleotide having the nucleotide sequence set forth in SEQ ID NO: 4; and
   (c) the third polynucleotide having the nucleotide sequence set forth in SEQ ID NO: 5, SEQ ID NO: 6 or SEQ ID NO: 7.

8. The nucleic acid molecule as claimed in claim 1, wherein the nucleic acid molecule additionally comprises between 2-7 binding sites for the tetracycline repressor protein.

9. The nucleic acid molecule as claimed in claim 1, wherein the mammalian cell is a mouse, rat, hamster, monkey or human cell.

10. An expression vector comprising the nucleic acid molecule as claimed in claim 1.

11. The expression vector as claimed in claim 10, wherein the expression vector is an adenoviral vector, a vaccinia or retroviral vector, a baculovirus vector, or a lentiviral vector.

12. The expression vector as claimed in claim 10, wherein the nucleic acid molecule is operably-linked to a heterologous polynucleotide.

13. A mammalian host cell comprising the expression vector as claimed in claim 10.

14. A kit comprising the mammalian host cell as claimed in claim 13, optionally together with one or more additional components selected from the group consisting of:
   (i) a helper plasmid;
   (ii) a virus genome plasmid;
   (iii) a buffer solution;
   (iv) a restriction enzyme; and
   (v) transfection media.

15. A kit comprising the expression vector as claimed in claim 10, optionally together with one or more additional components selected from the group consisting of:
   (i) a helper plasmid;
   (ii) a virus genome plasmid;
   (iii) a buffer solution;
   (iv) a restriction enzyme;
   (v) transfection media; and
   (vi) mammalian cells.

* * * * *

```
                           SEQUENCE LISTING

<160> NUMBER OF SEQ ID NOS: 7

<210> SEQ ID NO 1
<211> LENGTH: 433
<212> TYPE: DNA
<213> ORGANISM: Artificial Sequence
<220> FEATURE:
<223> OTHER INFORMATION: Synthetic promoter element

<400> SEQUENCE: 1
cgtgaggctc cggtgcccgt cagtgggcag agcgcacatc gcccacagtc cccgagaagt    60
tggggggagg ggtcggcaat tgaaccggtg cctagagaag gtggcgcggg gtaaactggg   120
aaagtgatgt cgtgtactgg ctccgccttt ttcccgaggg tgggggagaa ccgtatataa   180
gtgcactagt cgccgtgaac gtcaatggaa agtccctatt ggcgttacta tgggaacata   240
cgtcattatt gacgtcaatg acggtaaatg gcccgcctgg cattatgccc agtacatgac   300
cttatgggac tttcctactt ggcagtacat ctacgtatta gtcatcgcta ttaccatgct   360
gatgcggttt tggcagtaca tcaatgggcg tggatagcgg tttgactcac ggggatttcc   420
aagtctccac ccc                                                      433

<210> SEQ ID NO 2
<211> LENGTH: 172
<212> TYPE: DNA
<213> ORGANISM: Artificial Sequence
<220> FEATURE:
<223> OTHER INFORMATION: Synthetic promoter element

<400> SEQUENCE: 2
ctaccgggta ggggaggcgc ttttcccaag gcagtctgga gcatgcgctt tagcagcccc    60
gctgggcact tggcgctaca caagtggcct ctggcctcgc acacattcca catccaccgg   120
taggcgtcaa tggaaagtcc ctattggcgt tactatggga acatacgtca tt           172

<210> SEQ ID NO 3
<211> LENGTH: 106
<212> TYPE: DNA
<213> ORGANISM: Artificial Sequence
<220> FEATURE:
<223> OTHER INFORMATION: Synthetic promoter element

<400> SEQUENCE: 3
agtaatcaat tacggggtca ttagttcata gcccatatat ggagttccgc gttacataac    60
ttacggtaaa tggcccgcct ggctgaccgc ccaacgaccc ccgccc                  106

<210> SEQ ID NO 4
```

```
<211> LENGTH: 150
<212> TYPE: DNA
<213> ORGANISM: Artificial Sequence
<220> FEATURE:
<223> OTHER INFORMATION: Synthetic promoter element

<400> SEQUENCE: 4
attgacgtca atgggagttt gttttggcac caaaatcaac gggactttcc aaaatgtcgt      60
aacaactccg ccccattgac gcaaatgggc ggtaggcgtg tacggtggga ggtctatata     120
agcagagctg gtttagtgaa ccgtcagatc                                      150

<210> SEQ ID NO 5
<211> LENGTH: 157
<212> TYPE: DNA
<213> ORGANISM: Artificial Sequence
<220> FEATURE:
<223> OTHER INFORMATION: Synthetic promoter element

<400> SEQUENCE: 5
tgaagttggt ggtgaggccc tgggcaggtt ggtatcaagg ttacaagaca ggtttaagga      60
gaccaataga aactgggcat gtggagacag agaagactct tgggtttctg ataggcactg     120
actctctctg cctattggtc tattttccca cccttag                              157

<210> SEQ ID NO 6
<211> LENGTH: 333
<212> TYPE: DNA
<213> ORGANISM: Artificial Sequence
<220> FEATURE:
<223> OTHER INFORMATION: Synthetic promoter element

<400> SEQUENCE: 6
gcccaggaag tacacgagaa gctccgagga ttggctgaag tccaacgtct ctgattgcgg      60
tggctcagag cacccgtatc attttggagg tgagtggctt tggttcccgg ctgaggtgga    120
gtgggctgag gactagactg agccctcgga catggaggtg gggatggggc agactcatcc    180
cattcttgac caagcccttg ttctgctccc ttcccaggct ctgtgactgg gcaacctgc    240 aaggagctgg ccagccagcc tgacgtggac ggcttccttg tgggtggtgc ttccctcaag   300
cccgaattcg tggacatcat caacgccaaa caa                                  333

<210> SEQ ID NO 7
<211> LENGTH: 155
<212> TYPE: DNA
<213> ORGANISM: Artificial Sequence
<220> FEATURE:
<223> OTHER INFORMATION: Synthetic promoter element

<400> SEQUENCE: 7
gttgttcgct ttgataaact tccaggattc ggagacagta ttgaagctca ggtacagaaa      60
taatttcacc tttctttctc tttctattca gtgtggcaca tctgtaaacg ttcactcttc    120
acttagagac atcctcaacc aaatcaccaa accaa                                155
```